US008451972B2

(12) United States Patent
Dafni

(10) Patent No.: US 8,451,972 B2
(45) Date of Patent: May 28, 2013

(54) METHODS, CIRCUITS, DEVICES, APPARATUS, ASSEMBLIES AND SYSTEMS FOR COMPUTER TOMOGRAPHY

(75) Inventor: Ehud Dafni, Caesarea (IL)

(73) Assignee: Arineta Ltd., Caesarea (IL)

( * ) Notice: Subject to any disclaimer, the term of this patent is extended or adjusted under 35 U.S.C. 154(b) by 215 days.

(21) Appl. No.: 12/910,786

(22) Filed: Oct. 23, 2010

(65) Prior Publication Data

US 2011/0268246 A1    Nov. 3, 2011

Related U.S. Application Data

(60) Provisional application No. 61/279,571, filed on Oct. 23, 2009.

(51) Int. Cl.
*G01N 23/00* (2006.01)

(52) U.S. Cl.
USPC .................................. 378/8; 378/11

(58) Field of Classification Search
USPC ........................ 378/4, 8, 11, 12, 15
See application file for complete search history.

(56) References Cited

U.S. PATENT DOCUMENTS

| 6,504,893 | B1 * | 1/2003 | Flohr et al. ................. 378/8 |
| 7,672,423 | B2 * | 3/2010 | Proksa ....................... 378/11 |
| 7,983,385 | B2 * | 7/2011 | Heuscher et al. ............ 378/11 |

* cited by examiner

*Primary Examiner* — Jurie Yun
(74) *Attorney, Agent, or Firm* — Vladimir Sherman; Professional Patent Solutions

(57) ABSTRACT

Disclosed are methods, circuits, devices, assemblies and systems for performing Computer Tomography (CT)—for example of a periodically moving object such as a heart. According to some embodiments, there is provided a Computer Tomography scanner which includes an x-ray source adapted to generate an x-ray scan beam and a electromechanical assembly to which the x-ray source is mounted. The assembly may be adapted to move one or more electromechanical elements such that the scan beam is moved around the periodically moving object with a velocity profile having both constant and cyclically alternating rotational velocity components, and wherein the cyclically alternating velocity components are synchronized with the periodic motion of the object.

26 Claims, 11 Drawing Sheets

METHODS, CIRCUITS, DEVICES, APPARATUS, ASSEMBLIES AND SYSTEMS FOR COMPUTER TOMOGRAPHY

RELATED APPLICATIONS

The present application claims priority from U.S. Provisional Patent Application Ser. No. 61/279,571, filed on Oct. 23, 2009—which is hereby incorporated by reference in its entirety.

FIELD OF THE INVENTION

The present invention relates generally to the field of imaging by X-Ray Computer Tomography (CT). More specifically, the present invention relates to a method, apparatus, assembly and system for imaging of periodically moving subjects such as the human heart using a CT scanner.

BACKGROUND

Computed Tomography (CT) scanners are widely used in human and veterinary medicine, small animal scanning, industrial applications and homeland security. These scanners produce images of a subject by reconstruction of X ray attenuation data acquired over multiple view angles. Typically, a radiation source is rotated about the scanned subject and the X ray beam attenuated by the subject is measured by a detector array disposed opposite the source. Cross sectional or 3D images of the scanned subject are reconstructed from the attenuation data by algorithms known in the art as filtered back-projection or by other reconstruction methods.

Image reconstruction methods known in the art require attenuation data over at least a minimal angular range of the source relative to the subject. For example, filtered back-projection requires data over a continuous angular range of at least 180°+fan angle, where the fan angle is the beam angle covering the desired scan field of view.

Early generation CT scanners had a one dimensional detector array and were capable of scanning one axial slice of the subject at a time. More recent CT scanners have a two dimensional detector array comprising multiple rows of detector elements. These scanners, usually referred to as multislice or multidetector CT scanners, are capable of scanning multiple substantially parallel slices of the subject simultaneously. Further, CT scanners with a large number of detector rows are typically referred to as cone beam scanners. Cone beam scanners image a whole volume at a time.

Some CT scanners use a "step and shoot" protocol. In this protocol the gantry rotates about a stationary subject to generate a single or multiple axial images of the scanned subject, the subject is translated relative to the gantry, the gantry rotates again to generate images of an adjacent region, etc. Other CT scanners use a helical or spiral mode wherein the subject is being translated relative to the gantry while the gantry rotates and attenuation data is acquired.

Since CT scanning takes time, scanning subjects which move during the scan, may result in image blur and artifacts due to the subject's motion. Motion effects can be reduced by making the gantry rotation and data acquisition faster. Electron beam CT using electromagnetic steering of the X-ray source position rather than mechanical rotation, achieve even faster scan time.

Of particular interest are subjects which have periodic motion such as the human heart. The heart not only returns to approximately the same position every cycle, it also has particular phases in the cycle (e.g. late diastolic phase) in which the motion is minimal. Several solutions or combinations thereof are known in the art for CT imaging of the heart with motion freeze:

a. Spiral scan with retrospective gating—the source rotates about the subject at high rotation speed while the subject is translated axially at a relatively low pitch. X ray attenuation data and ECG data are acquired over multiple heart beats. The data is sorted after the scan and only data from ECG phases of minimal motion are used for reconstruction.

b. Spiral scan with prospective gating—same as above except the subject is translated axially at a very high pitch so that the entire heart is covered within a fraction of a heart beat. The one scanner available commercially that is using this mode (Siemens Definition Plus) is using dual sources and detectors to achieve the required coverage in a short time.

c. Axial scan with prospective gating—covering the required angular range in a single rotation and a single X ray shot gated by the ECG. The source rotation must be fast enough in order to be able to cover the entire angular range for image reconstruction within a fraction of a heart cycle. Data from multiple shots over consecutive heart beats may be added for improved statistics (e.g. in electron beam CT). Several shots over consecutive heart beats with patient translation between the shots may be applied to increase axial coverage ("step and shoot" protocol).

d. Multiple source rotations, each lasting multiple heart beats and acquiring non-continuous angular sectors of data during the desired heart phase, such that the multiple rotations provide together full angular coverage. ECG gating may be applied retrospectively or prospectively. The timing and speed of the rotations may be optimized according to heart rate.

Methods a through c above require a fast rotation high power CT scanner, which is expensive and costly to operate. Some of these methods apply more radiation dose than desired. Method d can be applied on a lower cost slower rotation scanner but the acquisition tends to take a long time. Considering for example a Siemens Artis C-arm operated in ECG gated "DynaCT" mode. The arm makes four 220° rotations of 5 sec each to acquire a total of 220° gated data in the desired heart phase. Considering about 2 sec for switching directions between rotations (the C-arm rotates back and forth), the procedure may take about 26 sec. In addition to heart motion, cardiac imaging is also sensitive to breathing motion, so cardiac imaging is preferably done during a breath stop. Many patients cannot hold their breath for 26 sec so the procedure is not applicable to them. In addition, the protocol is sensitive to irregularities in heart rate (arrhythmia).

Therefore, there is a need for a better apparatus and method for scanning the human heart or other periodically moving subjects.

SUMMARY OF THE INVENTION

The present invention includes methods, circuits, apparatus, devices, assemblies and systems for computed tomography (CT) imaging. According to some embodiments of the present invention, CT imaging of a periodically/cyclically moving object (e.g. organ such as a heart) may be performed during multiple sets of acquisition cycles, which acquisition cycles may be substantially synchronized with a given stage or phase in a complete motion cycle of the cyclically moving object (e.g. heart cycle phase in between contractions).

According to further embodiments of the present invention, each acquisition cycle may be associated with a different set of view angles.

According to some embodiments of the present invention, an imaging assembly may move a radiation emitting source in a first direction during an acquisition cycle such that multiple view angles may be acquired during a single imaging cycle. Data acquired over multiple acquisition cycles may be used to reconstruct a CT image. According to further embodiments of the present invention, the assembly may move the radiation emitting source in a second direction (e.g. same or opposite the first direction) in between acquisition cycles. According to yet further embodiments of the present invention, the assembly may include a primary and a secondary actuator, such that the primary actuator moves a primary frame of the assembly and the secondary actuator moves either: (1) an aperture of the radiation source, or (2) a support structure of the radiation source which is mounted on the primary frame. The support structure may be moved in the same or in a different direction relative to the movement of the primary frame.

According to embodiments, a Computer Tomography scanner for scanning a periodically moving object may include an x-ray source adapted to generate an x-ray scan beam. The scanner may include a electromechanical assembly to which said x-ray source is mounted, and the assembly may be adapted to move one or more electromechanical elements such that the scan beam is moved around the periodically moving object with a velocity profile having both constant and cyclically alternating rotational velocity components. The cyclically alternating velocity components of the velocity provide may be synchronized with the periodic motion. The assembly may include a rotatable frame which may be adapted to rotate at a substantially constant velocity during a scan. The rotatable frame may support a secondary beam moving structure adapted to move the beam with a cyclically alternating velocity relative to said rotatable frame. The secondary beam moving structure may be an X-ray source support bracket on a track. The secondary beam moving structure may be an electrically controllable X-Ray source comprising an anode which is adapted to emit X-rays from different points along the anode.

According to embodiments, the scanner may include a controller (i.e. control logic) adapted actuate at least a portion of said electromechanical assembly in response to output from a sensing circuit adapted to monitor a periodically moving object such as a heart (e.g. human heart). When the periodically moving object is a human heart, the sensing circuit may be an electrocardiogram circuit.

According to some embodiments, a Computer Tomography scanner for scanning a periodically moving object may include an x-ray source adapted to generate an x-ray scan beam. The scanner may also include an x-Ray detector adapted to acquire attenuation data relating to x-rays that were emitted by the source and attenuated by the object. A electromechanical assembly to which the x-ray source is mounted may be adapted to move the scan beam emitted from the source around the periodically moving object across at least 180° of substantially continuous viewing angles. Attenuation data may be acquired during a substantially common phase or stage of each of two or more complete motion cycles of the object, and attenuation data may not be acquired during other phases or stages of the motion cycles of the object.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
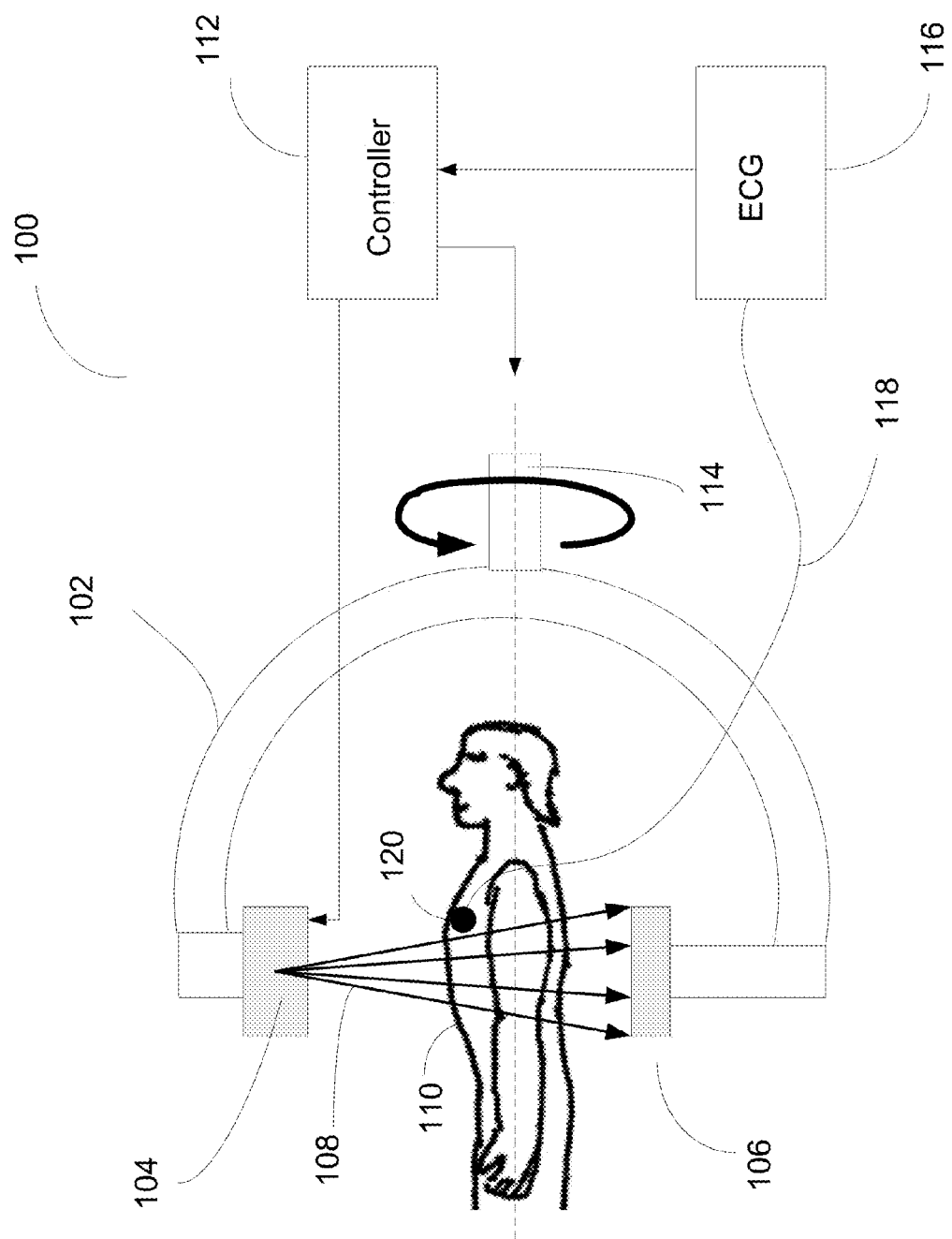
FIG. 1 shows a schematic exemplary description of the elements of a CT system according to some embodiments of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, components and circuits have not been described in detail so as not to obscure the present invention.

Unless specifically stated otherwise, as apparent from the following discussions, it is appreciated that throughout the specification discussions utilizing terms such as "processing", "computing", "calculating", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the inventions as described herein.

As described in the background, prior art scanners may be using a signal indicative of the imaged subject's motion (for example ECG) for gating the radiation and acquisition. Some prior art scanners may also optimize the rotation speed of the source according to heart beat rate. However, once rotation of the source commence, it stays approximately stable until the end of the rotation range. The present invention provides an apparatus, assembly, system and method for CT scanning of a periodically moving subject, wherein the scan angular range may be covered during multiple motion cycles of the scanned subject, and the radiation source may rotate about the subject at a variable rotation speed which may be synchronized with the periodic motion of the subject.

According to some embodiments of the present invention, there may be a moving subject which may be imaged by CT scanning. According to some embodiments of the present invention, the imaged moving subject may have a periodic type of motion (e.g. human heart). According to some embodiments of the present invention, the motion cycle period of the imaged subject may be substantially constant. According to some embodiments of the present invention, the motion cycle period of the imaged subject may vary.

According to some embodiments of the present invention, there may be a CT scanner for imaging a periodically moving subject constructed from a frame which may rotate around the imaged subject. According to some embodiments of the present invention, an X-ray source may be attached to the frame and an X-ray detector for detecting attenuated data of X-rays passing through the subject may be attached to the frame at a location substantially opposite the source. According to some embodiments of the present invention, the CT scanner may include a controller which may control the rotation of the frame and may activate the X-ray radiation and may also control its intensity. According to some embodiments of the present invention, the controller may control the data acquisition by the detector. According to some embodiments of the present invention, the attenuated data acquired by the detector may be reconstructed to images. According to some embodiments of the present invention, the set of reconstructed images may be processed and/or stored and/or displayed.

The present invention includes methods, circuits, apparatus, devices, assemblies and systems for computed tomography (CT) imaging. According to some embodiments of the present invention, CT imaging of a periodically/cyclically moving object (e.g. organ such as a heart) may be performed during multiple sets of acquisition cycles, which acquisition cycles may be substantially synchronized with a given stage or phase in a complete motion cycle of the cyclically moving object (e.g. heart cycle phase in between contractions). According to further embodiments of the present invention, each acquisition cycle may be associated with a different set of view angles.

According to some embodiments of the present invention, an imaging assembly may move a radiation emitting source in a first direction during an acquisition cycle such that multiple view angles may be acquired during a single imaging cycle. Data acquired over multiple acquisition cycles may be used to reconstruct a CT image. According to further embodiments of the present invention, the assembly may move the radiation emitting source in a second direction (e.g. same or opposite the first direction) in between acquisition cycles. According to yet further embodiments of the present invention, the assembly may include a primary and a secondary actuator, such that the primary actuator moves a primary frame of the assembly and the secondary actuator moves either: (1) an aperture of the radiation source, or (2) a support structure of the radiation source which is mounted on the primary frame. The support structure may be moved in the same or in a different direction relative to the movement of the primary frame.

According to embodiments, a Computer Tomography scanner for scanning a periodically moving object may include an x-ray source adapted to generate an x-ray scan beam. The scanner may include a electromechanical assembly to which said x-ray source is mounted, and the assembly may be adapted to move one or more electromechanical elements such that the scan beam is moved around the periodically moving object with a velocity profile having both constant and cyclically alternating rotational velocity components. The cyclically alternating velocity components of the velocity profile may be synchronized with the periodic motion. The assembly may include a rotatable frame which may be adapted to rotate at a substantially constant velocity during a scan. The rotatable frame may support a secondary beam moving structure adapted to move the beam with a cyclically alternating velocity relative to said rotatable frame. The secondary beam moving structure may be an X-ray source support bracket on a track. The secondary beam moving structure may be an electrically controllable X-Ray source comprising an anode which is adapted to emit X-rays from different points along the anode.

According to embodiments, the scanner may include a controller (i.e. control logic) adapted actuate at least a portion of said electromechanical assembly in response to output from a sensing circuit adapted to monitor a periodically moving object such as a heart (e.g. human heart). When the periodically moving object is a human heart, the sensing circuit may be an electrocardiogram circuit.

According to some embodiments, a Computer Tomography scanner for scanning a periodically moving object may include an x-ray source adapted to generate an x-ray scan beam. The scanner may also include an x-Ray detector adapted to acquire attenuation data relating to x-rays that were emitted by the source and attenuated by the object. A electromechanical assembly to which the x-ray source is mounted may be adapted to move the scan beam emitted from the source around the periodically moving object across at least 180° of substantially continuous viewing angles. Attenuation data may be acquired during a substantially common phase or stage of each of two or more complete motion cycles of the object, and attenuation data may not be acquired during other phases or stages of the motion cycles of the object.

FIG. 1 is a schematic presentation of some exemplary embodiments according to the present invention. System 100 may comprise a rotating frame 102 which may carry X-ray source 104 and detector 106. X-rays 108 emitted by source 104 may be attenuated while passing through scanned subject 110 and detected by detector 106. Controller 112 may activate the X radiation and may rotate the frame about axis 114. Attenuation data may be acquired over any required angular range relative to the scanned subject 110.

In the example of FIG. 1, system 100 is shown to have a "C-arm" shaped rotating frame 102. According to some embodiments of the present invention, the frame can be a rotating disk with a bore, through which the subject may be inserted, or any other form or shape known today or that may be devised in the future which may enable rotation of a source or a detector or both about a subject, or any other mechanism known today or that may be devised in the future which may enable circular or angular scanning of a subject. According to some embodiments of the present invention, the detector (for instance, 106 in the example shown in FIG. 1) can be a flat panel detector, pixilated array of scintillator crystals or any other detector which is known today or which may be devised in the future suitable for CT imaging. According to some embodiments of the present invention, the detector may be flat, arced around the X-ray focal spot or have any other curvature surface. According to the example shown in FIG. 1, system 100 is depicted as a third generation "rotate-rotate" scanner with a rotating detector. However, the invention is applicable also to a fourth generation CT with a stationary detector. According to some embodiments of the present invention, the detector may be stationary. According to some embodiments of the present invention, there may be a controller (112 in the example shown in FIG. 1) which may perform several tasks such as controlling the frame's rotation, controlling the X-ray radiation, controlling the attenuated data capture. According to some embodiments of the present invention, the controller may be a single controller or a set of several controllers, each performing one or more of the tasks.

In order to achieve clarity of the description, various parts common in CT scanners, such as gantry, subject support, data acquisition system, reconstruction computer, operator console and other commonly used parts, may be omitted from the description and drawings but may be included in the system described in embodiments of the present invention.

In a regular CT scan, the gantry is made to rotate at a substantially constant rotation speed and the X-ray intensity is substantially constant during the scan.

Figure 2:
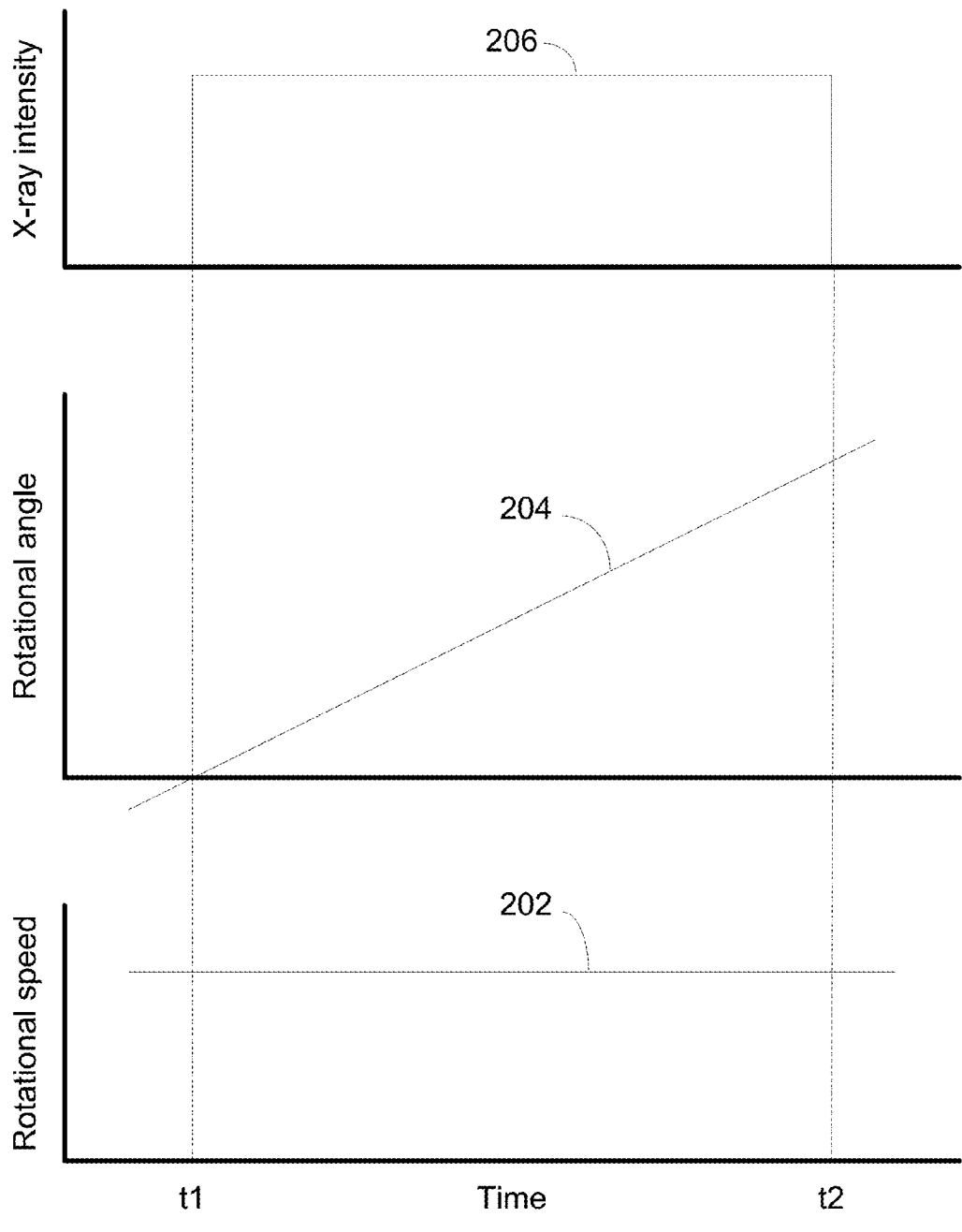
FIG. 2 shows the rotational speed and angle of the frame and the X-ray illumination intensity in existing CT systems.

FIG. 2. shows an example of the operation of a conventional CT scan. In this example, the scan starts at time t1 and ends at t2. Curve 202 shows the rotational speed vs. time during the scan, curve 204 is the angular position of the source and curve 206 is the X-ray intensity along the scan.

In order to enable the scan of a cyclically moving object, according to some embodiments of the present invention, a signal indicative of the object's motion may be applied to the CT scanner controller and may be used by the controller for synchronizing the scan. According to some embodiments of the present invention, the CT imaging may be performed during multiple sets of acquisition cycles, which acquisition cycles may be substantially synchronized with a given phase in the motion of the cyclically moving object. According to some embodiments of the present invention, the synchronization may include gating the attenuated data acquisition. According to some embodiments of the present invention, the synchronization may include controlling the X-ray radiation intensity. According to some embodiments of the present invention, the synchronization may include controlling the rotation of the frame. According to some embodiments of the present invention, the signal indicative of the object's motion may be derived from an ECG. According to some embodiments of the present invention, the signal indicative of the object's motion may be derived from a microphone.

In the example shown in FIG. 1, system 100 may be used to image the beating heart of a human patient. The system may comprise an ECG device 116 connected to subject 110 by at least one lead 118 and at least one electrode 120. ECG 116 may deliver a signal indicative of the heart's motion to controller 112 such that controller 112 can control the irradiation and/or the frame's rotation and/or the attenuated data acquisition, and/or any other element that may need to be synchronized with the signal, according to the signal. Other sources of signals synchronized with heart motion can be used. According to some embodiments of the present invention, the signal indicative of the object's motion may be derived from an acoustic microphone. For other periodically moving subjects (not human heart) other signals synchronized with the periodic motion of the subject can be provided instead of ECG 116 and used in a similar manner.

Figure 3A:
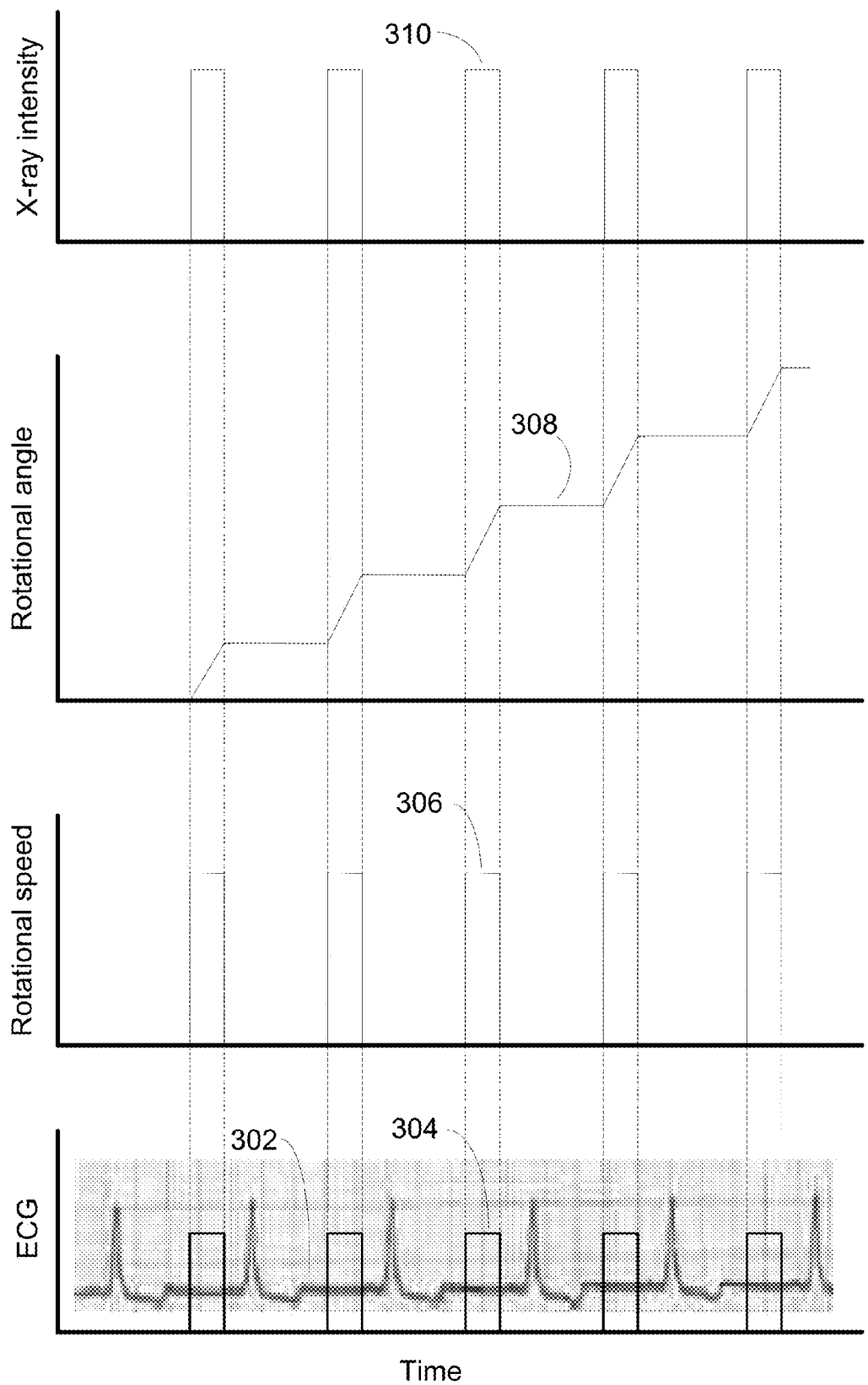
FIGS. 3a, 3b, 3c show several examples of the heart pulse with time windows for data acquisition, the frame speed and angle profile, and the X-ray illumination intensity profile according to some embodiments of the present invention.

FIG. 3a. is a description of the operation of an exemplary system according to some embodiments of the present invention. Curve 302 is a presentation of the ECG signal acquired by ECG device 116. A particular phase of the heart cycle considered suitable for CT acquisition, marked by rectangle 304, may define a data acquisition time slot for each heart beat. Time slots 304 may be determined by any of several algorithms, for example, it can be centered about a particular fraction of the beat to beat interval (measured from the QRS peak). A fraction of 0.7 is known to give good results. This algorithm may assume a relatively stable heart beat rate since the time slot 304 for a given heart beat may be extrapolated from previous beats. An alternative algorithm may determine 304 to be at a fixed delay from the QRS pulse, the delay may depend on the average heart beat rate. A person familiar with the art will appreciate that there may be other possible algorithms for determining the time slots 304. The determination of the time slots may be done by ECG unit 116 and/or controller 112. The time period between time slots 304 and the time width of each slot may not necessarily be fixed. For example, the controller may identify early heart beat during the time slot of the previous beat and close the time slot immediately. Further, the controller may skip one or several heart beats if it identifies rate irregularities.

According to some embodiments of the present invention, the device providing the signal indicative of the object's motion (e.g. ECG, microphone) may determine a timeslot suitable for acquiring attenuation data. According to some embodiments of the present invention, the controller may determine a timeslot suitable for acquiring attenuation data. According to some embodiments of the present invention, the timeslot may be centered about a particular fraction of the beat to beat interval (measured from the QRS peak). According to some embodiments of the present invention, the timeslot may be at a fixed delay from the QRS pulse. According to some embodiments of the present invention, the delay may depend on the average heart beat rate. According to some embodiments of the present invention, any algorithm known today or that may be devised in the future for determining the time slot may be used. According to some embodiments of the present invention, one or more heart beats may be skipped in a way that the interval between two heart beats may not include a timeslot.

According to some embodiments of the present invention, the controller may rotate the frame during a timeslot period and may halt the rotation between timeslots. According to some embodiments of the present invention, the rotation speed of the frame during a timeslot may be substantially constant. According to some embodiments of the present invention, the rotation speed of the frame during a timeslot may vary. According to some embodiments of the present invention, the controller may start rotating the frame prior to the start of a timeslot. According to some embodiments of the present invention, the controller may start rotating and accelerating the angular speed of the frame prior to the start of a timeslot, so that before or at the timeslot start, the frame may reach a predefined desired speed and/or angle. According to some embodiments of the present invention, at or after a timeslot end, the controller may decelerate the angular speed of the frame. According to some embodiments of the present invention, during the time in between timeslots, the controller may rotate the frame to the next acquisition start angle. According to some embodiments of the present invention, during the time in between timeslots, the controller may rotate the frame to an angle smaller than the next acquisition start angle. According to some embodiments of the present invention, during the time in between timeslots, the controller may rotate the frame back, in the opposite direction to the direction the frame may turn during acquisition. According to some embodiments of the present invention, during the time in between timeslots the controller may turn the frame back to an angle substantially equal to the angle in which the previous acquisition ended. According to some embodiments of the present invention, during the time in between timeslots the controller may turn the frame back to an angle smaller than the angle in which the previous acquisition ended.

According to some embodiments of the present invention, the controller may control the X-ray source radiation. According to some embodiments of the present invention, the controller may turn the radiation on during the timeslot periods, and turn it off in between timeslots. According to some embodiments of the present invention, the controller may turn the radiation on some time period before a timeslot start. According to some embodiments of the present invention, the controller may turn the radiation off some time period after a timeslot end. According to some embodiments of the present invention, the controller may turn the radiation on for the entire scanning period. According to some embodiments of the present invention, the radiation intensity may be substantially constant during a timeslot. According to some embodiments of the present invention, the radiation intensity may vary during a timeslot.

Curve 306 in FIG. 3a shows an example of the rotational speed that may be applied to frame 106 by controller 112. The frame rotation may be activated during time slots 304 and may be stopped between time slots, as shown by curve 306. Curve 308 is an exemplary presentation of the angular position of the frame as a function of time. The process may be repeated over multiple heart beats until the desired angular range may be covered. In some embodiments the radiation source may be activated during time slots 304, as shown by curve 310, and may be turned off between time slots 304. In some embodiments the radiation may be activated before the start of the time slots 304 and turned off after the end of the time slots to ensure stable radiation intensity during rotation and data acquisition. Yet in some embodiments the radiation may stay on also between time slots. This may be applicable for example in industrial scanning where there may be no need to reduce the radiation dose.

A specific case is described as an example. Assuming the scanned patient has a heart beat rate of 75 BPM, the average heart beat cycle time is 800 msec. We assume further for the sake of the example that the desired time window for acquisition is 200 msec in each heart beat. Assuming that an angular coverage of 220° is required in order to reconstruct images. A frame with a rotation speed of 15 RPM (90°/sec) may cover angular sectors of 18° during each time slot of 200 msec. Therefore, the total acquisition may be done over 13 heart beats and last 10.4 sec. For acquisition of 360° of data, 20 heart beats may be required over 16 sec.

Figure 3B:
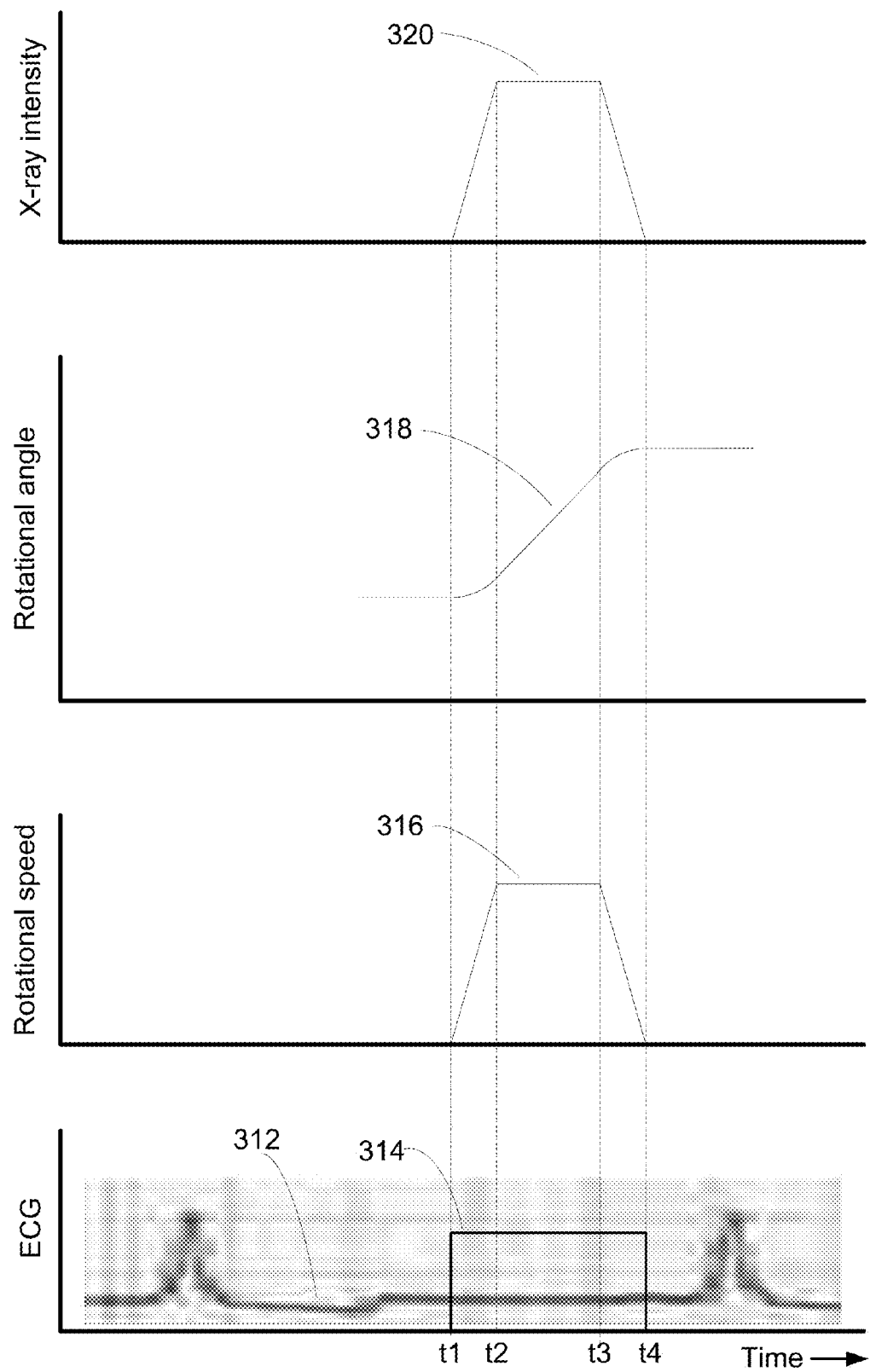

FIG. 3b shows an example of the system operation according to some embodiments of the present invention. The steps taken during a single cardiac cycle are shown, wherein the scan may comprise repetition of these steps over several heart beat cycles. Curve 312 describes the ECG signal and rectangle 314 marks a possible data acquisition time slot at the desired phase of the heart cycle, starting at time t1 and ending at time t4. As shown by curve 316, at t1, the controller may start to accelerate the frame angularly until time t2. Between time t2 and t3 the frame may rotate at a fixed rotational speed. From time t3 and until time t4 the frame may decelerate to a complete stop.

The rotational position corresponding to velocity profile 316 is shown by curve 318. It may be noted that at certain angles, at the start and the end of the rotational motion, the frame may spend more time per angle than it may at the high rotational speeds. For a system with fixed X-ray beam intensity during rotation and data acquisition (e.g. curve 310 in FIG. 3a), access of data statistics may result at the start and end of the frame's motion, with higher than needed radiation dose. Another anticipated effect may be non uniform noise in the resulted images. In exemplary embodiments according to FIG. 3b, the X-ray beam intensity may be changed during time slot 314 to reflect the time spent at each angle. Curve 320 shows exemplary X-ray intensity profile that may meet this condition.

The curves 316, 318 and 320 in FIG. 3b are shown as examples. Other curves may be also be applicable according to embodiments of the present invention.

Figure 3C:
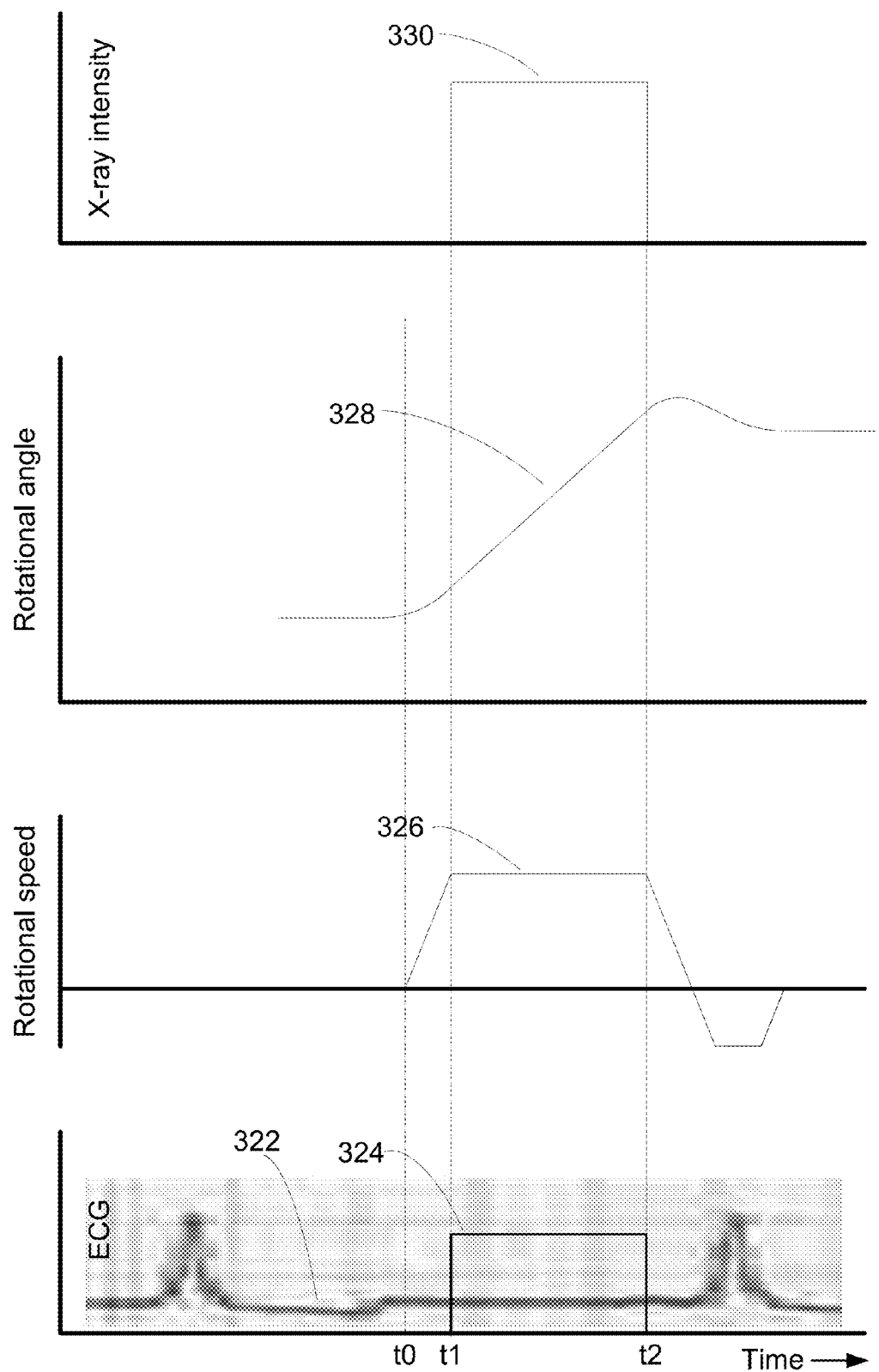

FIG. 3c is another exemplary description of the system operation according to some embodiments of the invention. The frame carrying the X-ray source may start angular acceleration at time t0, prior to the data acquisition time slot 324 which may start at time t1 and end at time t2. The angular velocity profile 326 may be designed such that at or before time t1 the X-ray source may reach the desired angular speed. At time t2 or at a later time during the cardiac cycle the frame may decelerate. According to the embodiments described in the example shown in this figure, the deceleration may continue until the frame may start rotating in the opposite direction. Eventually, after the frame retracts a certain angular range, it may stop and be prepared for the next cardiac cycle and next acceleration forward in a way that the source angular range may be covered continuously without gaps. This can be seen in curve 328. The X-ray source may be activated during the time slot 304 (curve 330) or at a wider time window. The advantage of embodiments according to FIG. 3c is that the time between acquisitions may be used for acceleration of the frame before acquisition and for retracting the frame at the end of each acquisition so that it may be ready for the next acceleration.

According to some embodiments, the rotation speed profile may be designed such that consecutive acquisitions may start substantially at the angle in which the previous acquisition ended. I this way, a continuous angular coverage may be achieved. According to other embodiments, the rotation speed profile may be designed in a way that consecutive acquisitions may start at a smaller angle than the angle the previous acquisition ended (with respect to the rotation direction). According to these embodiments, a partial angular overlap between data sectors may be achieved. Such overlap may be useful to assure seamless stitching between data acquired in sequential motion periods. According to some embodiments of the present invention, data may be acquired with some angular overlap, as described above, and reduced radiation intensity may be applied during the overlap regions.

FIG. 3a shows an example of data acquisition for adjacent angular sectors to be sequential while the frame may be rotating in the same direction. However, some embodiments of the invention may cover the desired angular range by covering angular sectors at other orders and in different directions. For example, angular coverage with gaps may be achieved during sequential heart beats, and the gaps may be covered in following heart beats while the frame may be rotating in the same or opposite direction.

According to some embodiments of the present invention, sequential angular sectors may be acquired sequentially. According to some embodiments of the present invention, angular sectors may be acquired at a predefined order. According to some embodiments of the present invention, angular sectors may be acquired at an order dependant on the heart beat. According to some embodiments of the present invention, the data acquisition may be done while the frame is turning in one direction. According to some embodiments of the present invention, the data acquisition may be done while the frame may be turning back and forth.

According to some embodiments of the present invention, the CT scanner may be constructed from a frame which may be able to rotate around the scanned subject. According to some embodiments of the present invention, the frame may have at least one track attached to it along part or its entire circumference. According to some embodiments of the present invention, the frame may have a track stretched between two points along the frame's circumference. According to some embodiments of the present invention, the frame may have a second track stretched between two other points along the frame's circumference. According to some embodiments of the present invention, the at least one track may be straight or have an arced shape or any other shape. According to some embodiments of the present invention, there may be at least one carriage which may be mounted on the at least one track. According to some embodiments of the present invention, the at least one carriage may be able to ride along the at least one track in either direction. According to some embodiments of the present invention, at least one carriage may carry an X-ray source. According to some embodiments of the present invention, at least one carriage may carry a collimator. According to some embodiments of the present invention, the X-ray source and the collimator may be attached to the same carriage. According to some embodiments of the present invention, at least one carriage may carry a detector. According to some embodiments of the present invention, the frame may rotate forwards and/or backwards and/or not rotate at all. According to some embodiments of the present invention, the carriage may ride on the track in the direction of the frame rotation, and/or opposite the frame's rotation direction. According to some embodiments of the present invention, the controller may control the rotation of the frame (direction, acceleration, speed) and/or the movement of the one or more carriages relative to the frame (direction, acceleration, speed). According to some embodiments of the present invention, the controller may move one or more carriages according to a predefined travel profile by simultaneously rotating the frame and moving the carriage relative to the frame. According to some embodiments of the present invention, the travel of the carriage may be synchronized with a signal indicative of the object's motion. According to some embodiments of the present invention, the controller may control the X-ray radiation (time, duration, intensity). According to some embodiments of the present invention, the controller may control the data acquisition.

According to some embodiments of the present invention, the function of the carriage may be performed by other types of members of the system, such as a sled sliding on the track. According to some embodiments of the present invention, there may be an actuator which may drive the carriage or sled or any other system member, relative to the frame. According to some embodiments of the present invention, the actuator may be controlled by the controller.

Figure 4A:
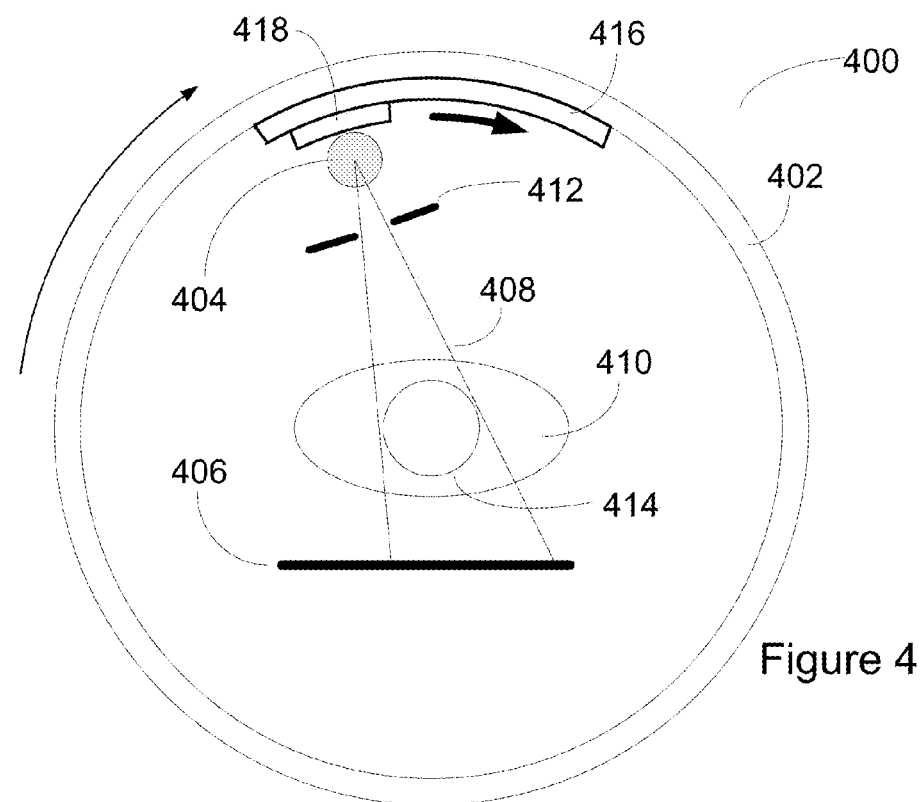
FIGS. 4a & 4b is a schematic exemplary description of part of the CT system showing the X-ray source movement mechanism and other parts of the system according to some embodiments of the present invention.

FIG. 4a is an exemplary illustration of other embodiments according to the present invention. System 400 may comprise a rotating frame 402, which may carry X-ray source 404 and detector 406 opposite the source. Source 404 may deliver X radiation beam 408 to scanned subject 410. Detector 406 may measure the attenuated radiation. Optionally, collimator 412 may be coupled to the X-ray source and may be used to direct the X-ray beam to a particular field of interest 414 within subject 410. According to some embodiments, the subject may be a human patient and the field of interest may include the human heart.

According to some embodiments of the present invention, frame 402 may comprise a section of circular track 416 and the X-ray source 404 may be mounted on carriage 418 which may be made to move along track 416 in the rotation direction of frame 402 and opposite the rotation direction of frame 402. According to some embodiments of the present invention, system 400 may comprise also a controller for controlling the rotational motion of the frame, the motion of the X-ray source relative to the frame and activation of the X-ray radiation. According to some embodiments of the present invention, system 400 may comprise an actuator for driving the rotational motion of the frame and/or an actuator for driving the motion of the X-ray source relative to the frame. According to some embodiments of the present invention, the one or more actuator may be controlled by the controller. According to some embodiments of the present invention, the system may be provided with a monitor for generating a signal synchronized with periodic motion of the scanned subject. According to some embodiments of the present invention, this monitor may be an ECG monitor. These parts of the system as well as other parts common to CT scanners are not shown in the drawing for clarity.

Some embodiments of the present invention may be explained by the operation of system 400 which is described below in reference to FIG. 4a and FIG. 4b. The operation of system 400 may refer to a periodically moving scanned subject wherein it may be desired to acquire attenuation data only at a certain time window in each motion cycle, corresponding to a particular phase in the cycle. During operation, the frame 402 of system 400 may rotate continuously at a certain frame speed.

FIG. 4a shows the system at time t1, the start of the acquisition time window. At that time, carriage 418, which may have been retracted to the back end of the track prior to time t1, may be accelerated so that the frame speed+carriage 418 speed relative to the frame, may yield a source speed higher than the frame speed. According to some embodiments of the present invention, the optional collimator 412 may be moved along with the X-ray source so the beam may keep being directed to the field of interest.

Figure 4B:
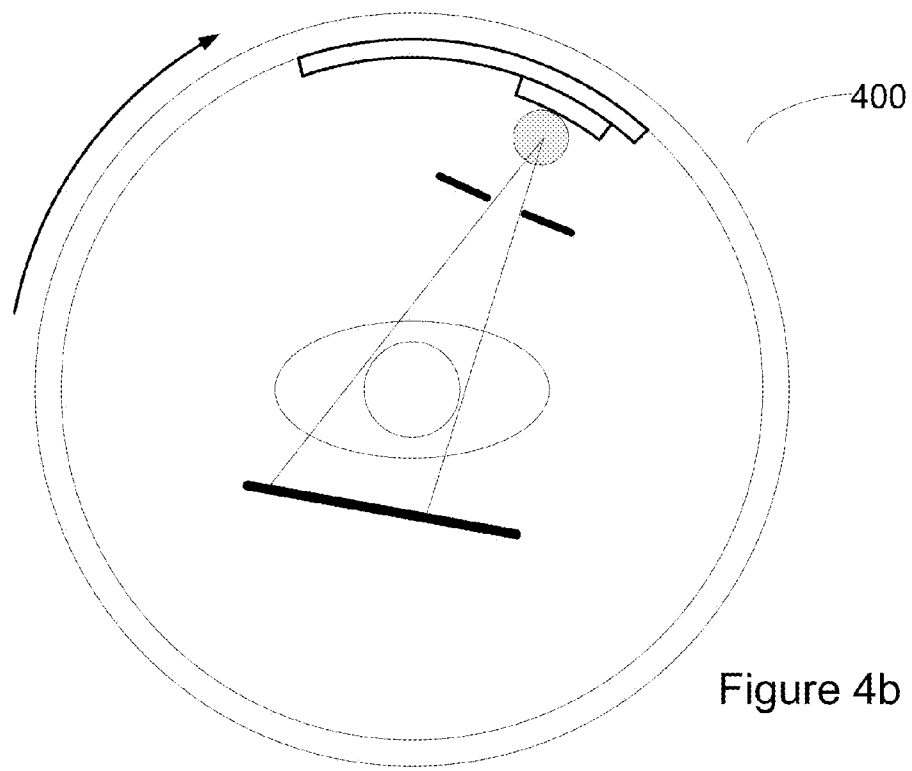

FIG. 4b shows the system at time t2, the end of the acquisition time window. At that time carriage 418, which may now be at the front end of the track, may be stopped from moving relative to the frame. During the time window from t1 to t2, the frame may have a certain angular increment whereas the X-ray source may have a larger angular increment than the frame with respect to the subject. Therefore a sector of data corresponding to the angular range covered by the source may be achieved. At the next stage, until the start of the next acquisition at the next motion cycle, the frame may keep rotating while the X-ray source may be retracted back to the back end of the track in anticipation for the next acquisition cycle. The process may be repeated multiple times until the desired angular range for image reconstruction may be covered.

Figure 4C:
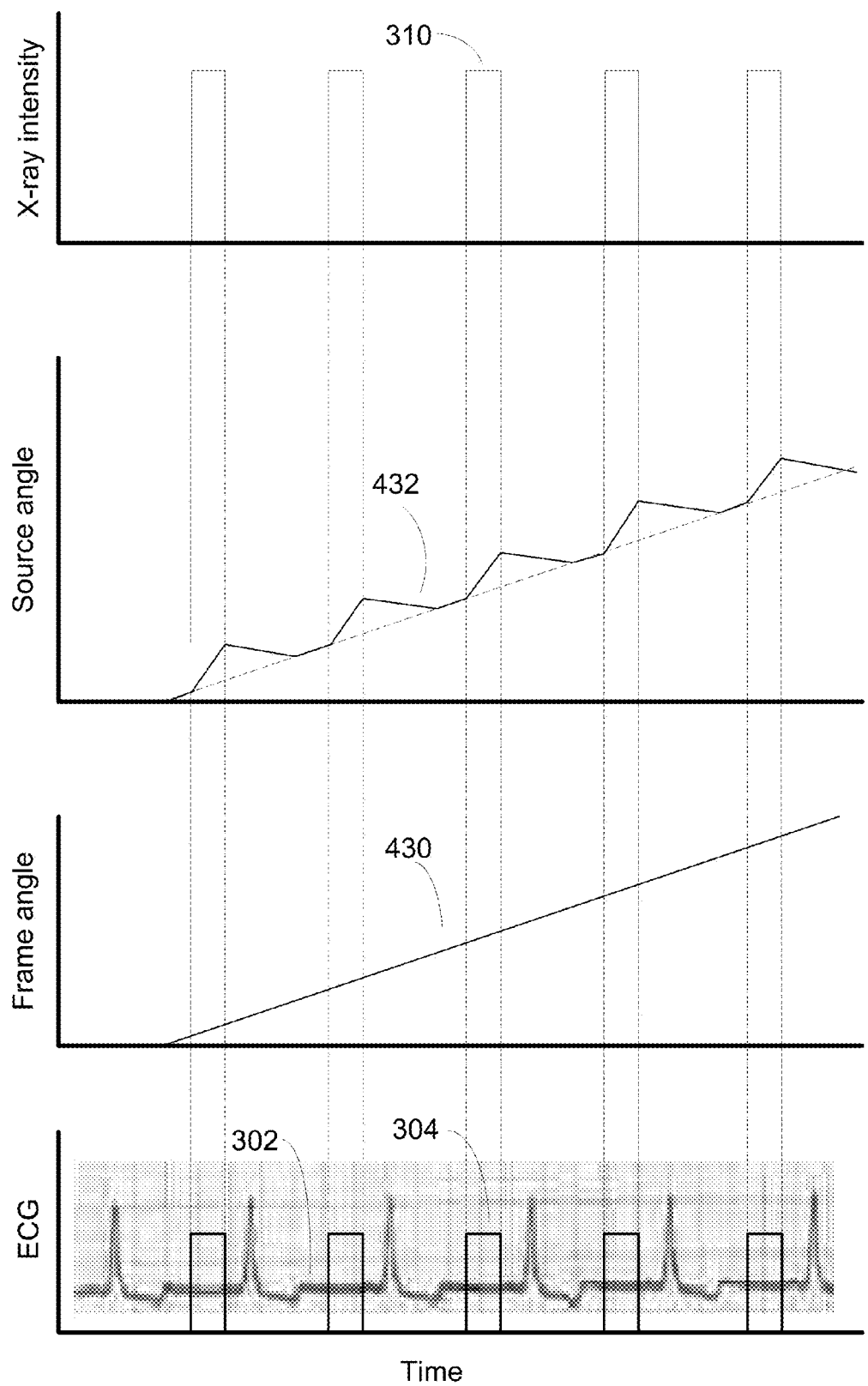
FIGS. 4c & 4d show several examples of the heart pulse with time windows for data acquisition, the frame speed and angle profiles, and the X-ray illumination intensity profile according to some embodiments of the present invention.

The operation can be understood also from FIG. 4c referring to cardiac scanning as an example. Curves 302, 304 and 310 have the same meaning as in FIG. 3a. Curve 430 is the angular position of the frame relative to the scanned subject. Curve 432 is the angular position of the X-ray source relative to the subject, where the dashed line next to it is the position of the frame (same as 430). It can be seen that the source rotates faster than the frame during acquisition time slots 304. Between acquisition time slots, the source retracts and follows the frame until the next time slot starts.

The time-angle diagrams of FIG. 4c are provided by way of example. According to some embodiments of the present invention, the source may start acceleration before the start of acquisition and may start deceleration when or after the acquisition ends. According to some embodiments, data may be acquired in partially overlapping angular sectors.

Figure 4D:
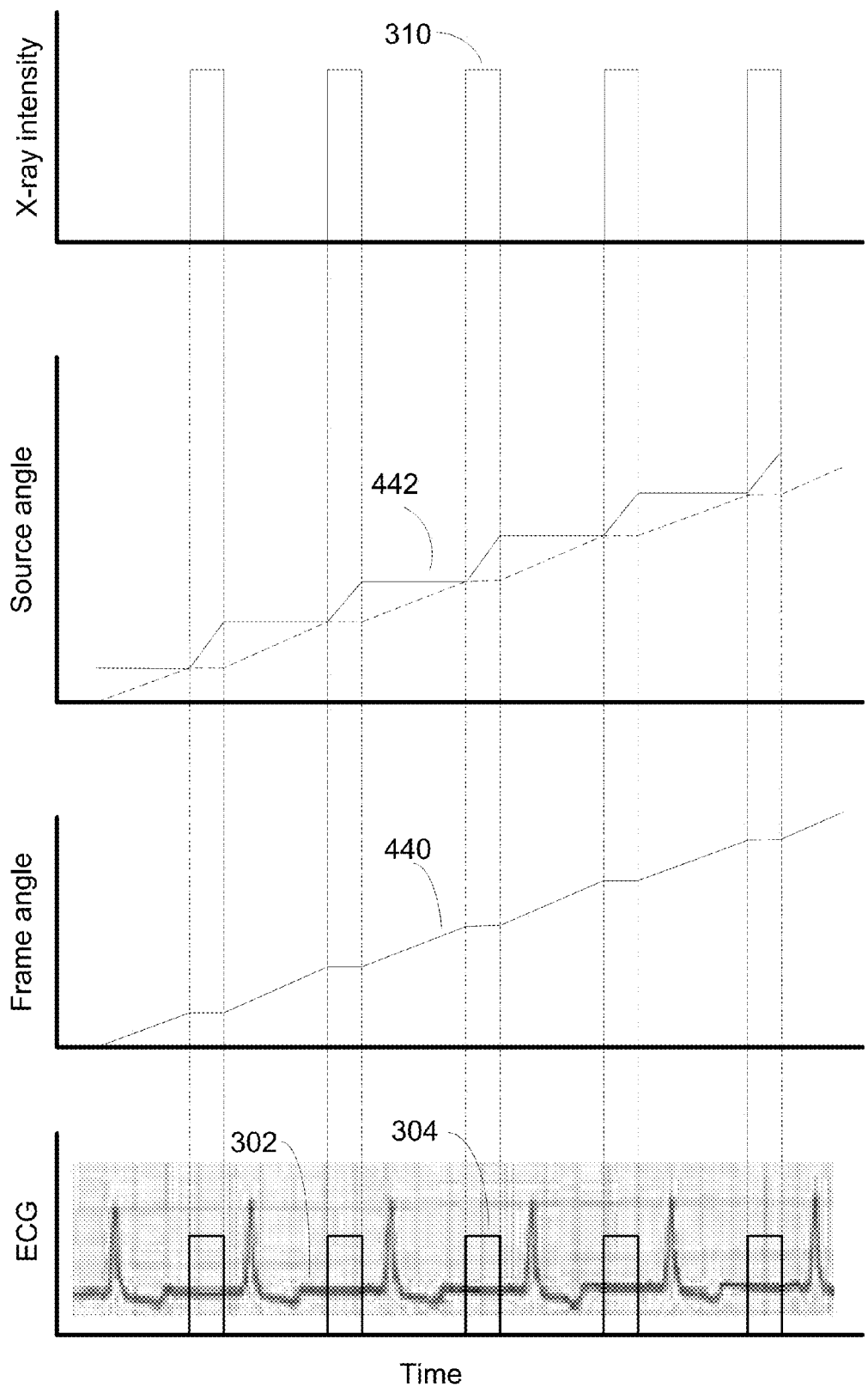

FIG. 4d shows another exemplary time-angle diagram according to some embodiments of the present invention. According to these embodiments the frame's movement may be halted during the acquisition time slots and may be incremented to the next start angle between time slots (curve 440). The X-ray source may be rotated at a high speed during acquisition time slots, and may be retracted relative to the frame between time slots (curve 442). FIG. 4a-4d are shown by way of examples. Other combinations of synchronized motions of the frame and the source may be applied to achieve coverage of the desired source angular range within the acquisition time slots.

Embodiments according to FIG. 4a-4d have the advantage that only the X-ray source (and the optional collimator), with a limited mechanical inertia, may be accelerated and decelerated to a high speed periodically, whereas the heavier frame which may have a high inertia may rotate at a substantially fixed rotation speed or may undergo smaller velocity changes.

Collimator 412 in FIG. 4a may optionally be used to limit the X-ray beam to the field of view of interest in the scanned subject. According to some embodiments of the present invention, the collimator may be mounted at a fixed orientation relative to the source and as the source is moving relative to the frame, the collimator may move with it and may stay directed at the field of view, as shown in FIG. 4a-4b. According to some embodiments, the collimator may change its orientation relative to the source but the collimator blades may be made to track the source motion so the beam may stay directed at the field of view. Further, according to some embodiments, the collimator blades may be adjusted dynamically during source motion so the X-ray beam may be directed at the entire width of the detector throughout the source motion. This alternative may provide attenuation data for parts of the subject which are outside the field of view of interest but which is still useful for image reconstruction. Further, according to some embodiments, a combination of a collimator and beam filter may be used so the field of view of interest may be illuminated with full radiation intensity and other parts of the subject may be illuminated with lower beam intensity.

In FIGS. 4a and 4b the source is shown to move relative to the frame on a sector of a circular track (an arc). According to some embodiments, the source may be mounted on a linear track or may have another trajectory of motion relative to the frame, while providing a range of view angles relative to the scanned subject during its movement relative to the frame.

Detector 406 in FIG. 4a is shown to have a flat surface. According to some embodiments of the present invention, other detector surfaces may be possible as well. According to these embodiments the detector may be wide enough (in the rotation plane) so as to cover the radiation transmitted through the volume of interest while the source may be moving relative to the frame. This goal may be achievable for a fourth generation scanner (stationary detector) and can be achieved in third generation CT (rotating detector) wherein the detector size may depend on the system geometry and the diameter of the field of view.

Figure 5A:
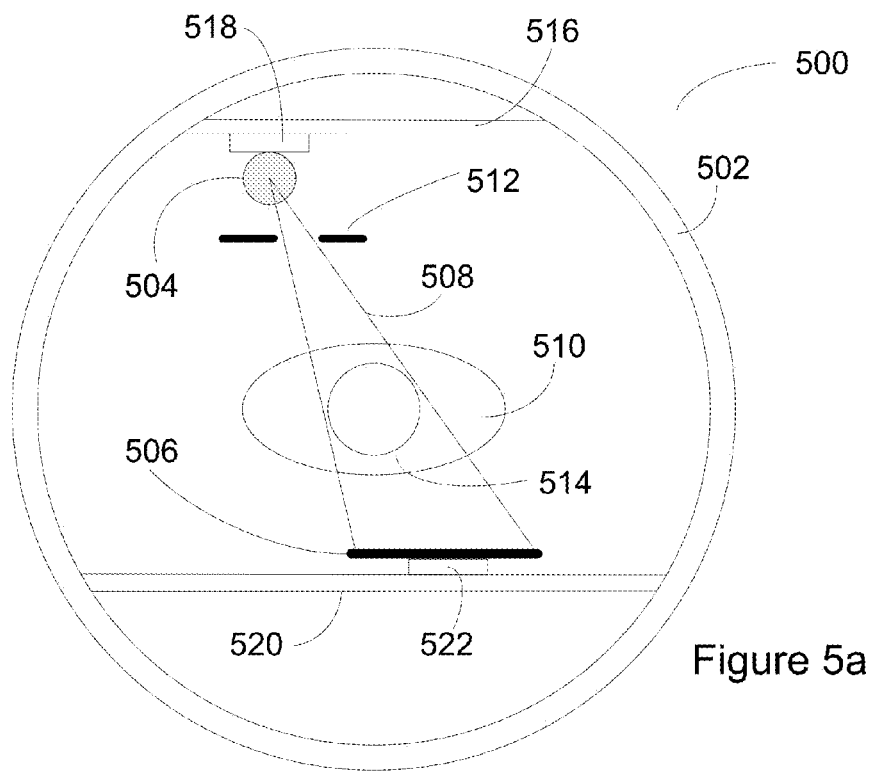
FIGS. 5a & 5b is a schematic exemplary description of part of the CT system showing the X-ray source movement mechanism and the detector movement mechanism as well as other parts of the system according to some embodiments of the present invention.

FIG. 5a is an illustration of some other embodiments according to the present invention, wherein the detector may be narrower than the detector in the embodiments described above with respect to the rotation plane. System 500 may comprise a rotating frame 502, which may carry X-ray source 504 and may also carry detector 506 opposite the source 504. Source 504 may deliver X radiation beam 508 to scanned subject 510, and detector 506 may measure the attenuated radiation. Optionally, collimator 512 may be coupled to X-ray source 504 and may be used to direct the X-ray beam to a particular field of interest 514 within subject 510. According to some embodiments, the subject may be a human patient and the field of interest may include the human heart.

Further, frame 502 may comprise track 516 and the X-ray source 504 may be mounted on carriage 518 which may be made to move along track 516 in a direction which may be tangent to the rotation direction of frame 502. Likewise, track 520 can be used for moving detector 506 which may be mounted on carriage 522. System 500 may comprise a controller which may control the rotational motion of the frame, and may also control the motion of the X-ray source and detector relative to the frame, and may also control the alignment of the collimator relative to the source and subject, and may also control the activation of X-rays. According to some embodiments of the present invention, system 500 may comprise an actuator for driving the rotational motion of the frame, and/or an actuator for driving the motion of the X-ray source relative to the frame, and optionally an actuator for driving the motion of the detector relative to the frame. According to some embodiments of the present invention, the one or more actuator may be controlled by the controller. According to some embodiments of the present invention, the system may be provided with a monitor for generating a signal which may be synchronized with periodic motion of the scanned subject. According to some embodiments, this monitor may be an ECG monitor. These parts of the system as well as other parts common to CT scanners are not shown in the figures for clarity purposes.

Some embodiments of the present invention may be explained by the operation of system 500 which is described below in reference to FIG. 5a and FIG. 5b. The operation of system 500 may refer to a periodically moving scanned subject wherein it may be desired to acquire attenuation data only at a certain time window in each periodic motion cycle, corresponding to a particular phase in the cycle.

FIG. 5a shows the system at time t1, the start of the acquisition time window. At that time carriage 518, which may have been retracted to the back end of the track prior to time t1, may be accelerated to a desired speed and X-ray radiation may be activated. Subsequently, data may be acquired over a sector of view angles of source 504 relative to the scanned subject 510. According to some embodiments of the present invention, the optional collimator 512 may be moved along with the X-ray source. According to some embodiments of the present invention, detector 506 which may be at one end of track 520 at time t1 may be made to move in the opposite direction to the source so radiation transmitted through the field of view may impinge on the detector surface throughout the acquisition.

Figure 5B:
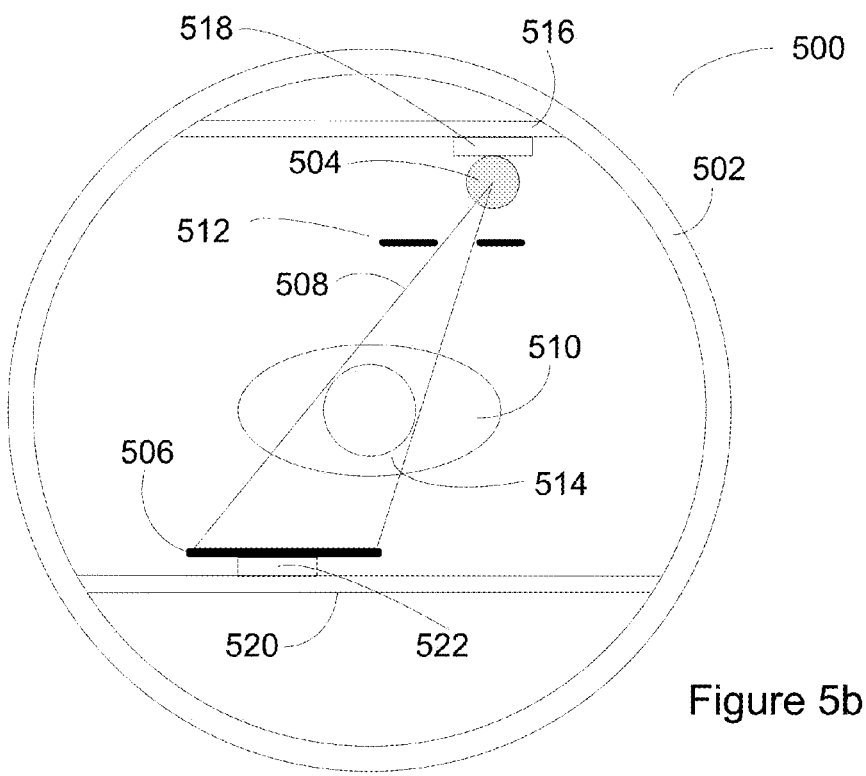

FIG. 5b shows the system at time t2, the end of the acquisition time window. At that time carriages 518 and 522, which may be at the ends of the respective tracks, may be stopped from moving relative to the frame. In this particular example the frame may be static during the acquisition time window. At the next stage, until the start of the next acquisition at the next motion cycle, the frame may rotate to the next start angle while the X-ray source and detector may be retracted to the back ends of the tracks in anticipation for the next acquisition cycle. The process may be repeated multiple times until the desired angular range for image reconstruction may be covered.

According to some embodiments of the present invention, other time-angle profiles may be applicable as well. According to some embodiments of the present invention shown in the examples of FIG. 5a-5b the frame may rotate at a substantially constant speed throughout the sequence, while the source and detector may be moved relative to the frame according to the subject motion phase. According to some embodiments of the present invention, tracks 516 and 520 may be linear or may have an arc like shape or may have a shape which may provide other motion trajectories.

Systems 400 and 500 described in FIGS. 4a-4b, and 5a-5b comprise an X-ray source which may be mechanically moveable relative to the frame.

According to some embodiments of the present invention, the X-ray source may be comprised of a vacuum tube which may include an anode and a cathode. According to some embodiments of the present invention, an electron beam may be emitted from the cathode and accelerated towards the anode. According to some embodiments of the present invention, the anode may have a flat or a curved front surface. According to some embodiments of the present invention, the vacuum tube may include electrostatic electrodes which may deflect the electron beam by applying a voltage to the electrodes. According to some embodiments of the present invention, the vacuum tube may include electromagnetic coils which may deflect the electron beam by applying a voltage to the coils. According to some embodiments of the present invention, the electrostatic electrodes' or electromagnetic coils' voltage may be controlled by a controller. According to some embodiments of the present invention, the controller may apply a voltage which may sweep the beam across the anode. According to some embodiments of the present invention, the beam may be swept once during a timeslot. According to some embodiments of the present invention, the beam may be swept multiple times during a timeslot. According to some embodiments of the present invention, the cathode may be moved mechanically in parallel to the anode plane. According to some embodiments of the present invention, the controller may control the cathode movement. According to some embodiments of the present invention, the controller may sweep the cathode (and therefore the beam) across the anode. According to some embodiments of the present invention, the cathode may be constructed from a plurality of electron beam emitters. According to some embodiments of the present invention, the controller may control the order in which the emitters may emit the electron beam. According to some embodiments of the present invention, the controller may cause the emitters to emit sequentially.

Figure 6A:
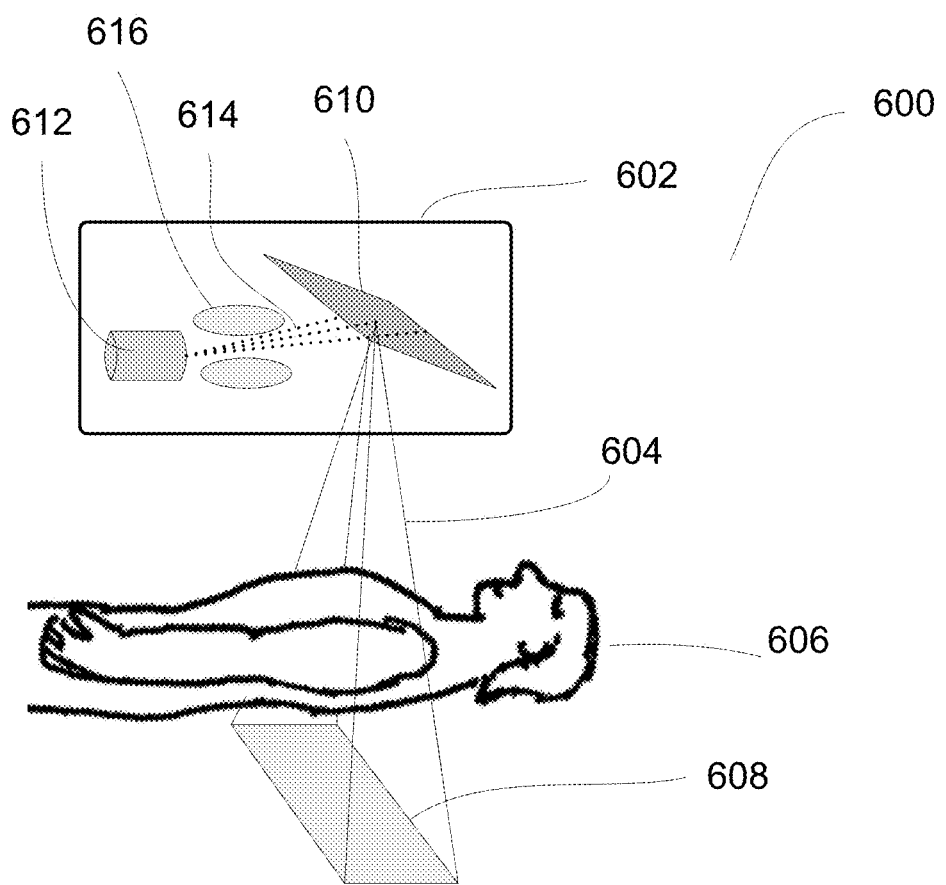
FIG. 6a is a schematic exemplary description according to some embodiments of the present invention of an electrostatic deflection of an X-ray beam source.

According to some embodiments of the present invention illustrated schematically in FIG. 6a, the X-ray focal spot may be movable relative to the frame electronically. System 600 may comprise an X-ray source 602 which may deliver X-ray beam 604 to patient 606 and detector 608. The X-ray source may comprise a vacuum enclosure in which there may be an anode 610 with a front surface which may be elongated in a direction tangent to the frame rotation and cathode 612. The front surface may be flat (as shown in FIG. 6a) or curved. Electron beam 614 which may be emitted from the cathode may be accelerated to the anode and may result in the emission of X-rays from a focal spot. According to some embodiments of the present invention, electrostatic electrodes 616 may be activated to sweep the electron beam and the position of the focal spot relative to variable voltage that may be applied by a controller (not shown). As the focal spot is swept across the anode during an acquisition time window, it may provide attenuation data across a sector of view angles relative to the subject. In other aspects the operation of system 600 may be similar to the operation of systems 400 or 500. The combination of the fast sweep of the focal spot during time windows and slow frame rotation may provide the required continuous angular coverage during multiple subject motion cycles.

System 600 may have the benefit of electronic rather than mechanical motion of the focal spot. The focal spot sweep can be very fast, which may enable narrow acquisition time windows. According to some embodiments of the present invention, the beam may be swept once during the acquisition time window. According to some other embodiments of the present invention, the beam may be swept multiple times during the acquisition time window. According to some embodiments of the present invention, the trajectory of the focal spot relative to the subject may be a straight line or an arc like or have any other shape. The anode and electrodes geometry depicted in FIG. 6a are shown by way of example, according to embodiments of the invention other geometries may be used, including, for example, rotating anodes. According to some embodiments of the present invention, sweeping of the electron beam and the focal spot may be done by magnetic steering rather than electrostatic steering.

Figure 6B:
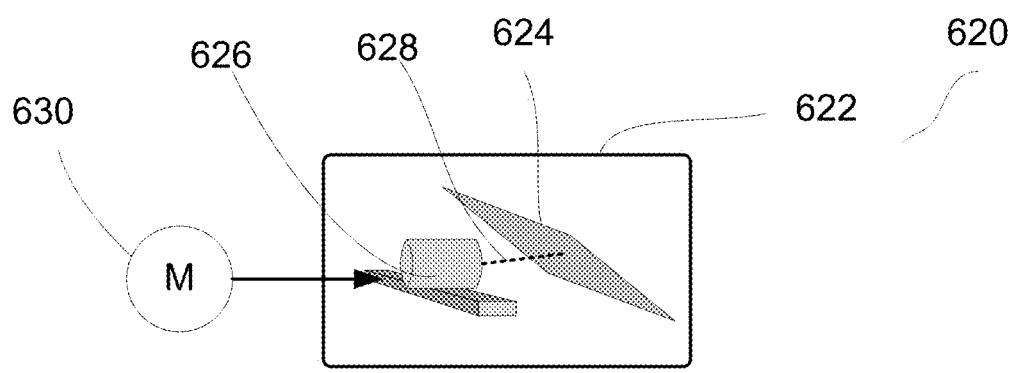
FIG. 6b is a schematic exemplary description according to some embodiments of the present invention of a mechanical deflection of an X-ray beam source.

FIG. 6b is an exemplary illustration of an alternative X-ray source 620 with a vacuum enclosure 622 wherein anode 624 may have a similar structure and function to anode 610 in FIG. 6a, and cathode 626 may be used to deliver electron beam 628 to the anode. According to some embodiments of the present invention, the cathode in source 620 may be movable on a track by motion control and drive 630. Source 620 may be used in a similar manner to source 602 of FIG. 6a, where focal spot sweeping may be achieved by mechanical sweeping of the cathode facing the anode. The advantage of these embodiments relative to embodiments in which the whole X-ray source may be moving relative to the frame, is that only the small mass of the cathode may need to be accelerated to a high speed.

Figure 6C:
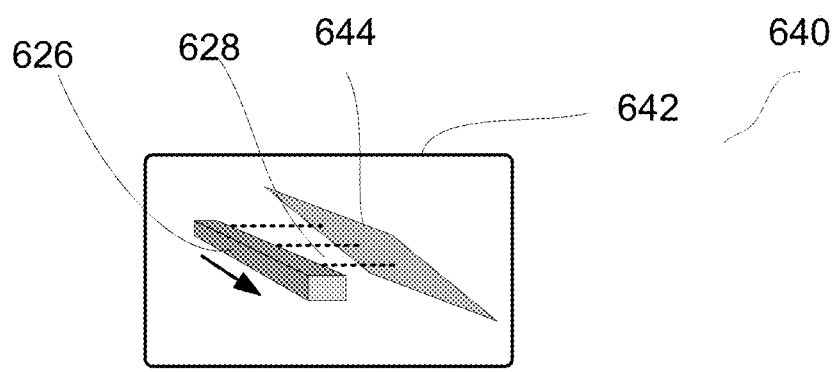
FIG. 6c is a schematic exemplary description of an array of electron beam emitters which may be used to sweep an X-ray beam according to some embodiments of the present invention.

FIG. 6c is an exemplary illustration of another alternative X-ray source according to some embodiments of the present invention. X-ray source 640 may comprise a vacuum enclosure 642, anode 644 and cathode 626 which may deliver electron beams 628. The cathode may comprise a linear array of electron sources which may be operated in sequence to generate the effect of focal spot sweeping. According to some embodiments of the present invention, the cathode may comprise an array of carbon nanotube based electron sources.

According to some embodiments of the present invention, source 602 may use X-ray source such as 620 described in FIG. 6b. or 640 described in FIG. 6c.

The invention was described with reference to various embodiments, each with certain features. Other embodiments with some of these features or a different combination of the features are also included within the scope of the invention.

The invention is described with reference to a cone beam geometry where the entire axial range of interest may be covered in a single axial position of the subject or in reference to fan beam geometry where only part of the axial range of interest may be covered in a single position of the subject and the subject may have to be translated axially relative to the frame to achieve full coverage. The invention is also described with reference to multiple source scanners where the variable speed source rotation may be applied to all or some of the multiple sources.

The invention is described with reference to a circular trajectory of the source about the subject. However it may be applicable also for non circular trajectories, e.g. spiral trajectories and other trajectories in which the source may also translate axially relative to the subject.

While certain features of the invention have been illustrated and described herein, many modifications, substitutions, changes, and equivalents will now occur to those skilled in the art. It is, therefore, to be understood that the appended claims are intended to cover all such modifications and changes as fall within the true spirit of the invention.

DESCRIBE FIGURES

While certain features of the invention have been illustrated and described herein, many modifications, substitutions, changes, and equivalents will now occur to those skilled in the art. It is, therefore, to be understood that the appended claims are intended to cover all such modifications and changes as fall within the true spirit of the invention.

What is claimed:

1. A Computer Tomography scanner for scanning a periodically moving object exhibiting a periodic motion, said scanner comprising:
    an x-ray source adapted to generate an x-ray scan beam; and
    a electromechanical assembly to which said x-ray source is mounted adapted to move one or more electromechanical elements such that said x-ray source is rotated around the periodically moving object with a velocity profile having both constant and cyclically alternating rotational velocity components in the same direction, and wherein said cyclically alternating velocity components are synchronized with said periodic motion.

2. The scanner according to claim 1, wherein said assembly comprises a rotatable frame.

3. The scanner according to claim 2, wherein said rotatable frame is adapted to rotate at a substantially constant velocity during a scan.

4. The scanner according to claim 2, wherein said rotatable frame supports a secondary X-ray source moving structure adapted to move the beam with a cyclically alternating velocity relative to said rotatable frame.

5. The scanner according to claim 4, said secondary X-ray source moving structure is an x-ray source support bracket on a track.

6. The scanner according to claim 4, said secondary X-ray source moving structure is an electrically controllable x-ray source comprising an anode wherein said source is adapted to emit x-rays from different points along the anode.

7. The scanner according to claim 1, further comprising control logic adapted to actuate at least a portion of said electromechanical assembly in response to output from a sensing circuit adapted to monitor the periodically moving object.

8. The scanner according to claim 7, wherein said periodically moving object is a heart.

9. The scanner according to claim 8, wherein said periodically moving object is a human heart and said sensing circuit is an electrocardiogram circuit.

10. A method of computer tomography scanning of a periodically moving object exhibiting a periodic motion, said method comprising:
    generating an x-ray scan beam from a source; and moving one or more electromechanical elements such that the x-ray source is rotated around the periodically moving object with a velocity profile having both constant and cyclically alternating rotational velocity components in the same direction, and such that said cyclically alternating velocity components are synchronized with said periodic motion.

11. The method according to claim 10, wherein moving one or more electromechanical elements includes moving a rotatable frame.

12. The method according to claim 11, wherein the rotatable frame is moved at a substantially constant velocity during a scan.

13. The method according to claim 11, wherein moving one or more electromechanical elements includes moving a secondary X-ray source moving structure adapted to move the beam with a cyclically alternating velocity relative to said rotatable frame.

14. The method according to claim 13, wherein the secondary X-ray source moving structure is an x-ray source support bracket on a track.

15. The method according to claim 13, wherein the secondary X-ray source moving structure is an electrically controllable x-ray source comprising an anode wherein said source is adapted to emit x-rays from different points along the anode.

16. The method according to claim 10, further comprising monitoring the motion of the periodically moving object.

17. The method according to claim 16, wherein the periodically moving object is a heart.

18. The method according to claim 17, wherein the periodically moving object is a human heart and monitoring includes using an electrocardiogram.

19. A Computer Tomography scanner for scanning a periodically moving object comprising:
    an x-ray source adapted to generate an x-ray scan beam;
    a detector adapted to acquire attenuation data relating to x-rays that were emitted by said source and attenuated by the object; a electromechanical assembly to which said x-ray source is mounted and adapted to rotate the x-ray source around the periodically moving object across at least 180 degree of substantially continuous viewing angles, wherein said rotation across at least 180 degree of viewing angles lasts longer than a period of the object periodic motion, and wherein attenuation data is acquired during a substantially single common phase or stage of each of two or more complete motion cycles of the object.

20. The scanner according to claim 19, wherein said electromechanical assembly comprises a rotatable frame adapted to rotate at a substantially constant velocity during a scan.

21. The scanner according to claim 20, wherein said rotatable frame supports a secondary X-ray source moving structure adapted to move the beam with a cyclically alternating velocity relative to said rotatable frame.

22. The scanner according to claim 21, wherein said secondary X-ray source moving structure is an x-ray source support bracket on a track.

23. The scanner according to claim 21, said secondary X-ray source moving structure is an electrically controllable x-ray source comprising an anode wherein said source is adapted to emit x-rays from different points along the anode.

24. The scanner according to claim 19, further comprising control logic adapted to actuate at least a portion of said electromechanical assembly in response to output from a sensing circuit adapted to monitor the periodically moving object.

25. The scanner according to claim 24, wherein said periodically moving object is a heart.

26. The scanner according to claim 25, wherein said periodically moving object is a human heart and said sensing circuit is an electrocardiogram circuit.

* * * * *